(12) United States Patent
Veis

(10) Patent No.: US 11,534,331 B2
(45) Date of Patent: Dec. 27, 2022

(54) ADJUSTABLE SLEEP APNEA ORAL APPLIANCE

(71) Applicant: SELANE PRODUCTS, INC., Chatsworth, CA (US)

(72) Inventor: Rob Veis, Chatsworth, CA (US)

(73) Assignee: ODIN SLEEP, LLC, Chatsworth, CA (US)

( * ) Notice: Subject to any disclaimer, the term of this patent is extended or adjusted under 35 U.S.C. 154(b) by 321 days.

(21) Appl. No.: 15/780,227

(22) PCT Filed: Nov. 30, 2016

(86) PCT No.: PCT/US2016/064291
§ 371 (c)(1),
(2) Date: May 30, 2018

(87) PCT Pub. No.: WO2017/095971
PCT Pub. Date: Jun. 8, 2017

(65) Prior Publication Data
US 2018/0353321 A1    Dec. 13, 2018

Related U.S. Application Data

(60) Provisional application No. 62/261,243, filed on Nov. 30, 2015.

(51) Int. Cl.
*A61F 5/00*    (2006.01)
*A61F 5/56*    (2006.01)
(Continued)

(52) U.S. Cl.
CPC ............... *A61F 5/566* (2013.01); *A61C 7/08* (2013.01); *A61C 7/36* (2013.01)

(58) Field of Classification Search
CPC .......... A61F 5/56; A61F 5/566; A61F 5/0006; A61C 7/06; A61C 7/08; A61C 7/10;
(Continued)

(56) References Cited

U.S. PATENT DOCUMENTS 6,604,527 B1 *   8/2003   Palmisano ............... A61C 7/08
                                                    128/848
8,517,029 B2     8/2013   Nelissen
(Continued)

FOREIGN PATENT DOCUMENTS

WO    2012158368 A1    11/2012
WO    2015144374       2/2015

OTHER PUBLICATIONS

Nishi, Yasuhiro; Tsuru, K; Kishita, C; Kamashita, Y; Hamano, T; Nagaoka, E. (2008). Effect of different labio-lingual spaces in tray designs on the displacement of and pressure against a mobile tooth. Journal of oral rehabilitation. 35. 700-5.10.1111/j. 1365-2842.2007. 01810.x. (Year: 2008).*

(Continued)

*Primary Examiner* — Adam Baker
(74) *Attorney, Agent, or Firm* — Loza & Loza, LLP; Michael F. Fedrick

(57) ABSTRACT

An oral appliance having an upper tray, a lower tray, and axial inserts attached to the upper tray to adjust the relative position of a user's upper jaw and lower jaw in order to treat sleep apnea and/or snoring while at the same time allowing orthodontic treatment of the subject.

9 Claims, 10 Drawing Sheets

(51) Int. Cl.
*A61C 7/08* (2006.01)
*A61C 7/36* (2006.01)

(58) Field of Classification Search
CPC .. A61C 7/12; A61C 7/14; A61C 7/141; A61C 7/143; A61C 7/36; A63B 71/085
USPC ............... 128/848, 859, 861, 862; 433/6, 19
See application file for complete search history.

(56) References Cited

U.S. PATENT DOCUMENTS

| | | | |
|---|---|---|---|
| 8,839,793 B2 | 9/2014 | Diaz | |
| 9,655,695 B2 | 5/2017 | Ross | |
| 9,820,882 B2 | 11/2017 | Liptak et al. | |
| 2009/0032030 A1 | 2/2009 | Callender | |
| 2010/0129763 A1* | 5/2010 | Kuo | A61C 7/36 128/861 |
| 2012/0227750 A1 | 9/2012 | Tucker | |
| 2012/0247485 A1 | 10/2012 | Timmons | |
| 2013/0112210 A1 | 5/2013 | Stein | |
| 2013/0269712 A1 | 10/2013 | Awde | |
| 2014/0020691 A1* | 1/2014 | Sweeney | A61F 5/566 128/848 |
| 2014/0076332 A1 | 3/2014 | Luco | |
| 2014/0326252 A1* | 11/2014 | Quaka | A61F 5/566 128/848 |
| 2015/0075540 A1* | 3/2015 | Dye | A61F 5/566 128/848 |
| 2016/0184129 A1* | 6/2016 | Liptak | A61F 5/566 128/848 |
| 2018/0168845 A1* | 6/2018 | Hofmann | A61F 5/566 |

OTHER PUBLICATIONS

International Preliminary Report on Patentability for International Patent Application No. PCT/US2016/064291, dated Jun. 5, 2018, 5 pages.
International Search Report and Written Opinion for International Patent Application No. PCT/US2016/064291, dated Mar. 30, 2017, 6 pages.
Anonymous, "Treatment of Obstructive Sleep Apnea and Snoring," SomnoMed: Preventing Snoring and Obstructive Sleep Apnea, retrieved on Jul. 19, 2018 from http://www.somnomed.com:80/somnomed-solution.html (2 pages).
European Search Report for European Application No. 16871456.6, dated Feb. 7, 2020, 8 pages.
Search Report for corresponding Chinese Patent Application No. 201680080432.5 dated Jan. 6, 2020.

* cited by examiner

ADJUSTABLE SLEEP APNEA ORAL APPLIANCE

CROSS-REFERENCE TO RELATED APPLICATIONS

This application is the U.S. national stage of International Patent Application No. PCT/US2016/064291, filed on Nov. 30, 2016 and titled ADJUSTABLE SLEEP APNEA ORAL APPLIANCE, which claims the benefit of priority under 35 U.S.C. § 120 from U.S. Patent Application No. 62/261,243, filed Nov. 30, 2015 and titled ADJUSTABLE SLEEP APNEA ORAL APPLIANCE. The disclosures of the foregoing applications are incorporated herein by reference in their entirety.

BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

Subjects are generally at greater risk for sleep apnea if they are overweight or have conditions such as diabetes, hypertension, or chronic nasal congestion. There are a variety of factors, however, which can lead to sleep apnea. One factor is the presence of a narrow maxilla and/or mandible in a subject. Maxillary constriction may increase nasal resistance and alter the tongue posture, leading to narrowing of the retroglossal airway. Constriction of the maxilla and/or the mandible generally reduces intraoral air volume and tends to force the tongue back into the posterior airway space, leading to obstructive sleep apnea during sleep.

Orthodontics is a field of dentistry which focuses on the repositioning of a subject's teeth and jaws for aesthetic or other reasons, for example due to the "overcrowding" of a subject's teeth. Orthodontic methods typically require a subject to make continuous use of a dental appliance for a period of time in order to achieve results. The use of such appliances precludes the concurrent use of currently available oral appliances for treating sleep apnea. There remains a need therefore for improved devices and methods for treating sleep apnea in users of orthodontic appliances who experience sleep apnea.

FIGURES

SUMMARY

Figure 1:
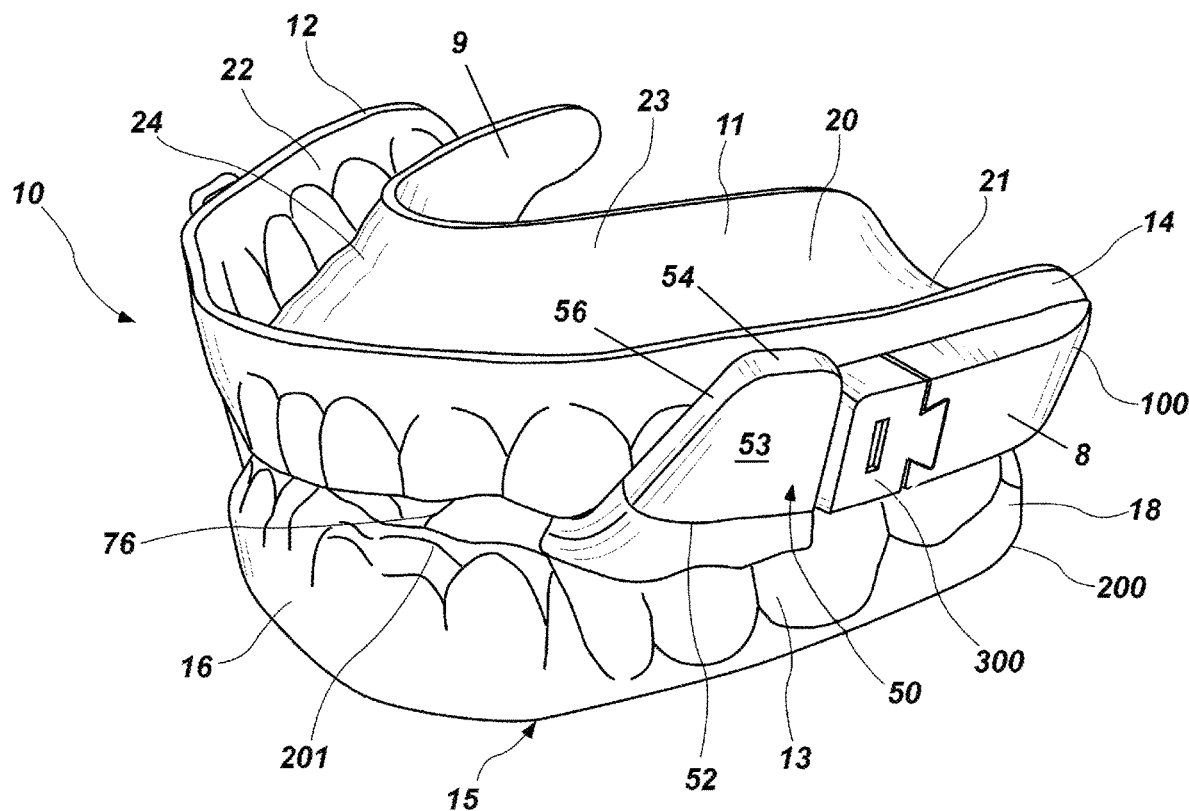
FIG. 1 is a left side, upper perspective view of the upper and lower portions of the present appliance, fitted together and ready for use.
Figure 2:
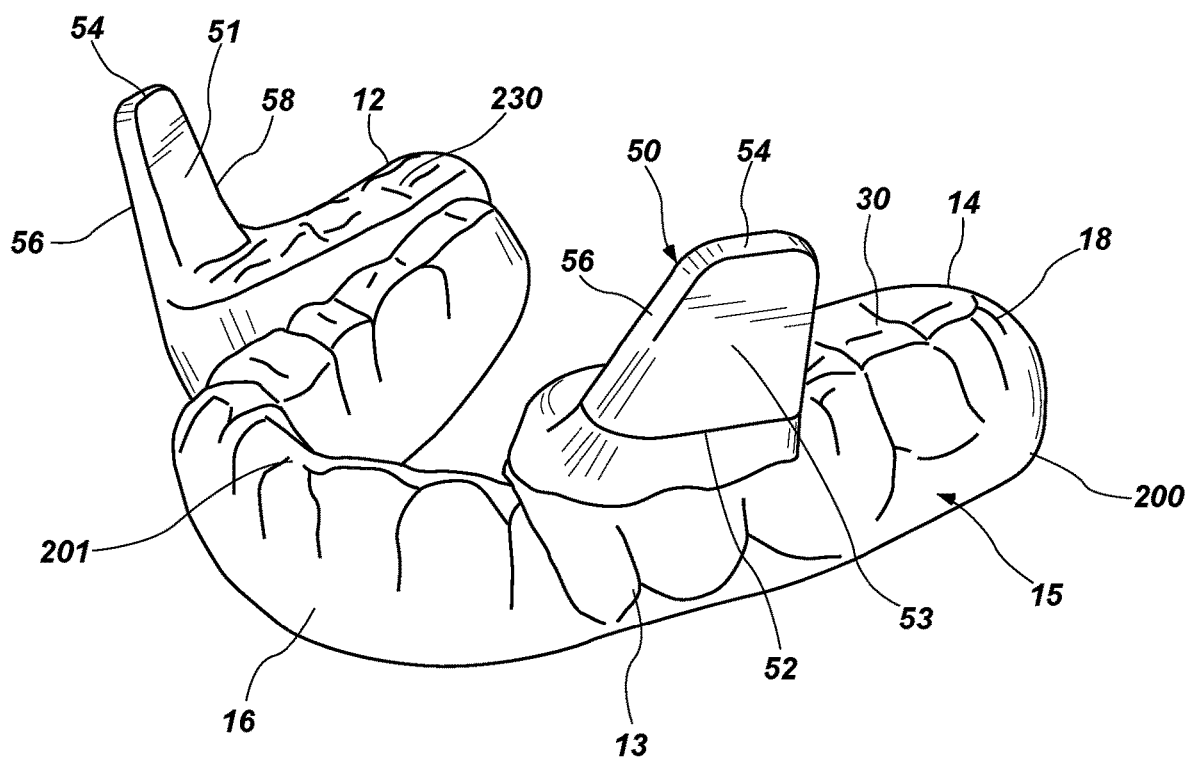
FIG. 2 is a left side, upper perspective view of the lower portion of the present appliance.
Figure 3:
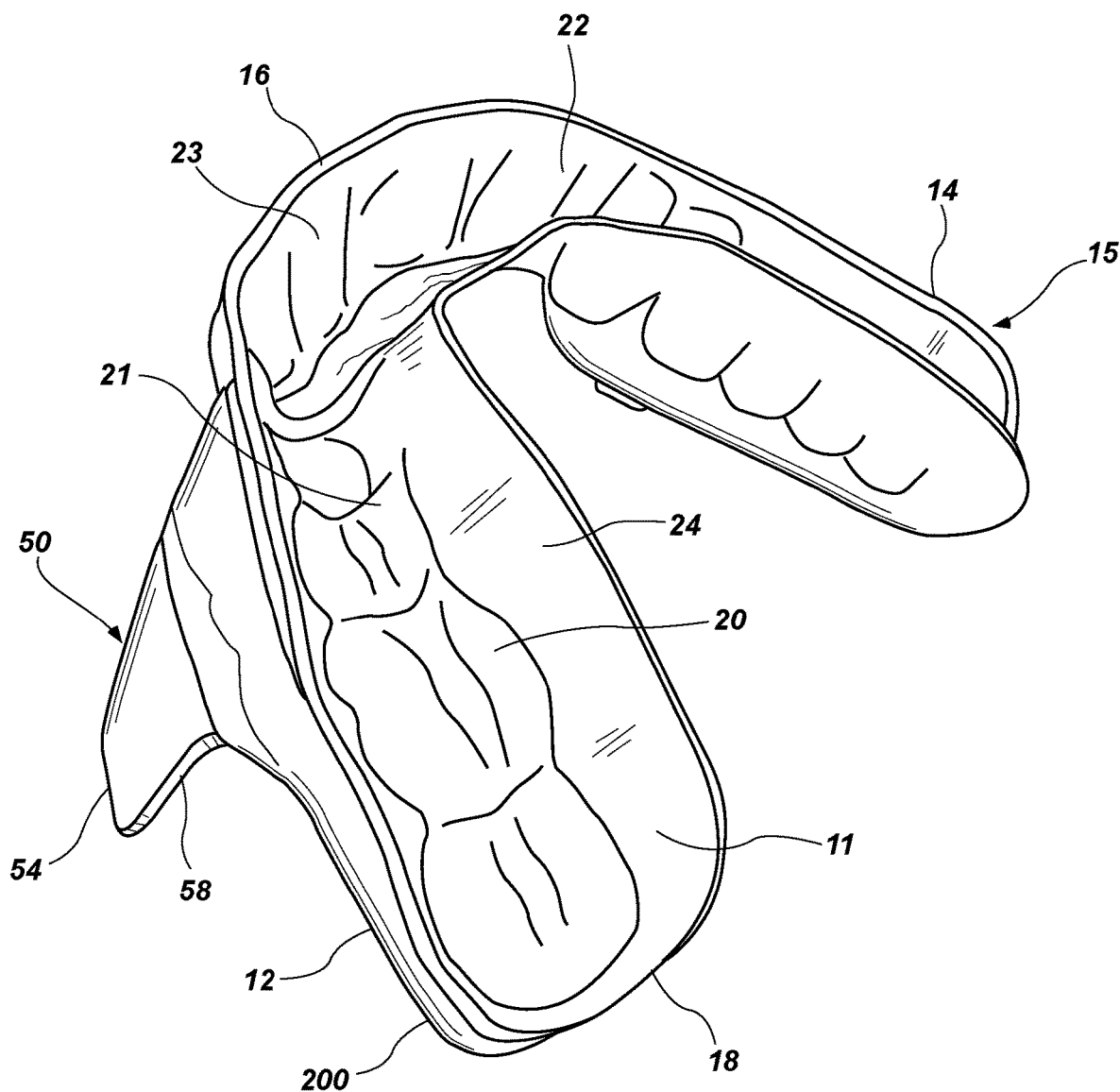
FIG. 3 is a right side, lower perspective view of the lower portion of the present appliance.
Figure 4:
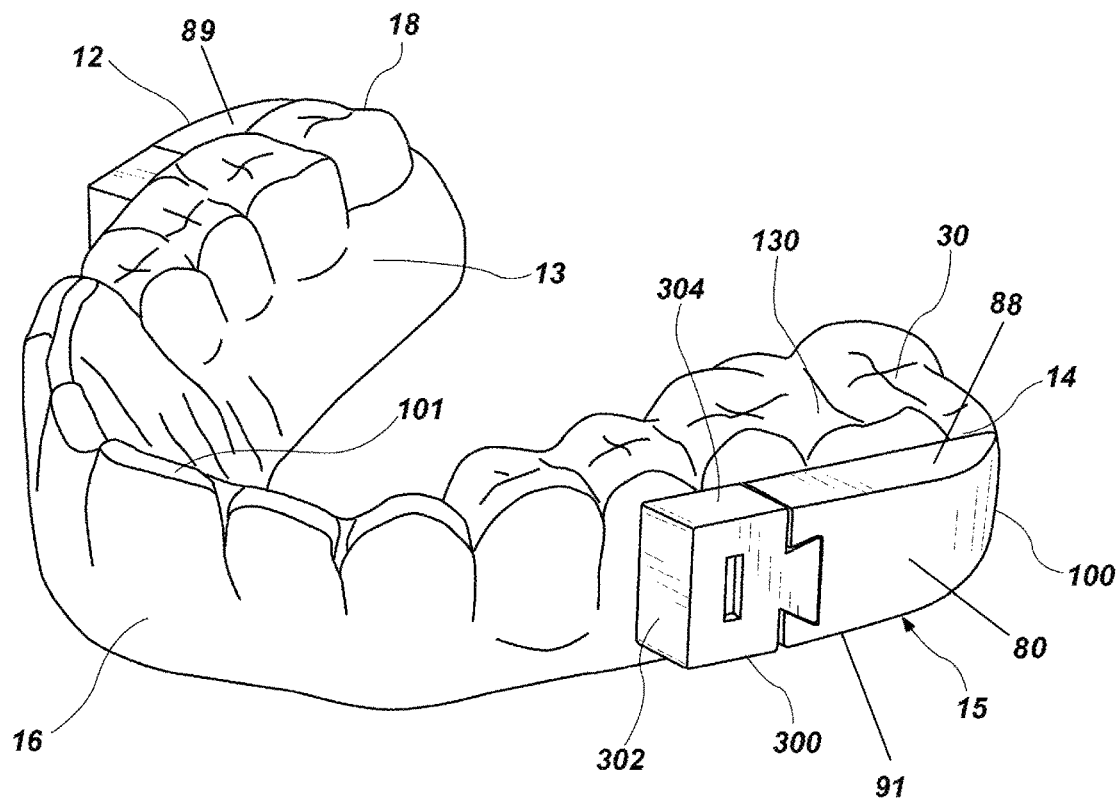
FIG. 4 is a right side, lower perspective view of the upper portion of the present appliance.
Figure 5:
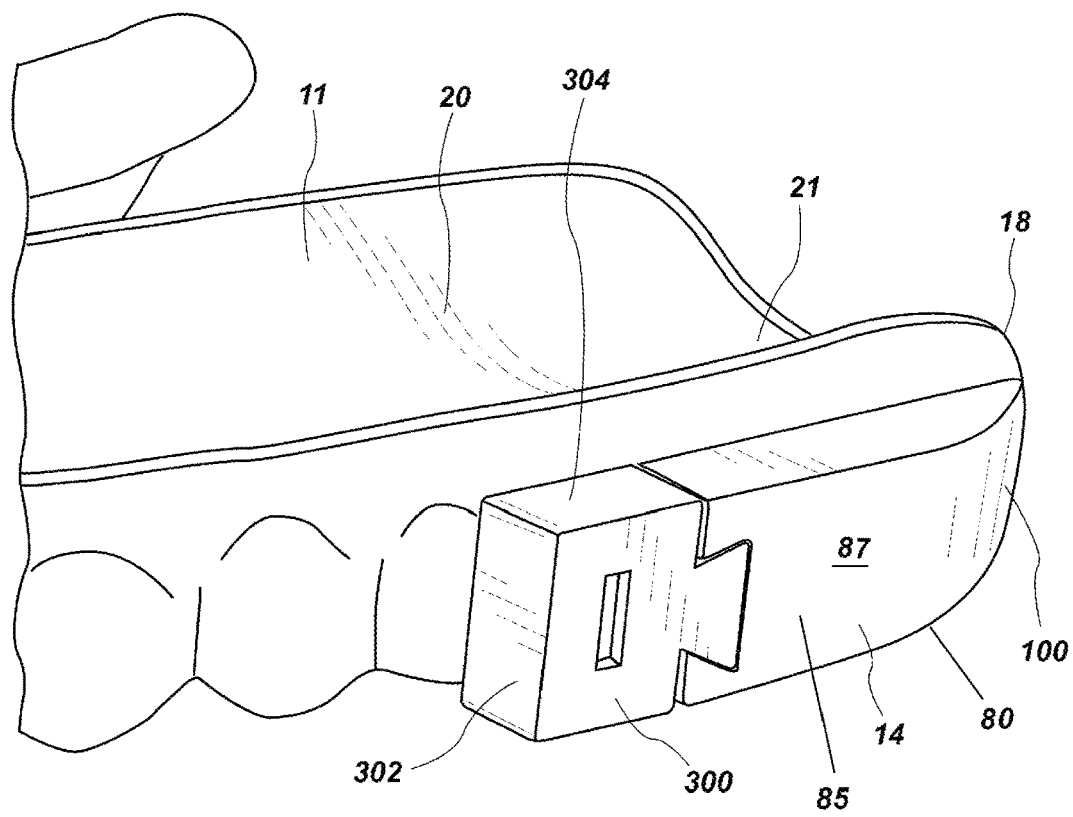
FIG. 5 is a right side, lower perspective view of the posterior portion of the upper appliance shown in FIG. 4, showing the attached insert portion.
Figure 6:
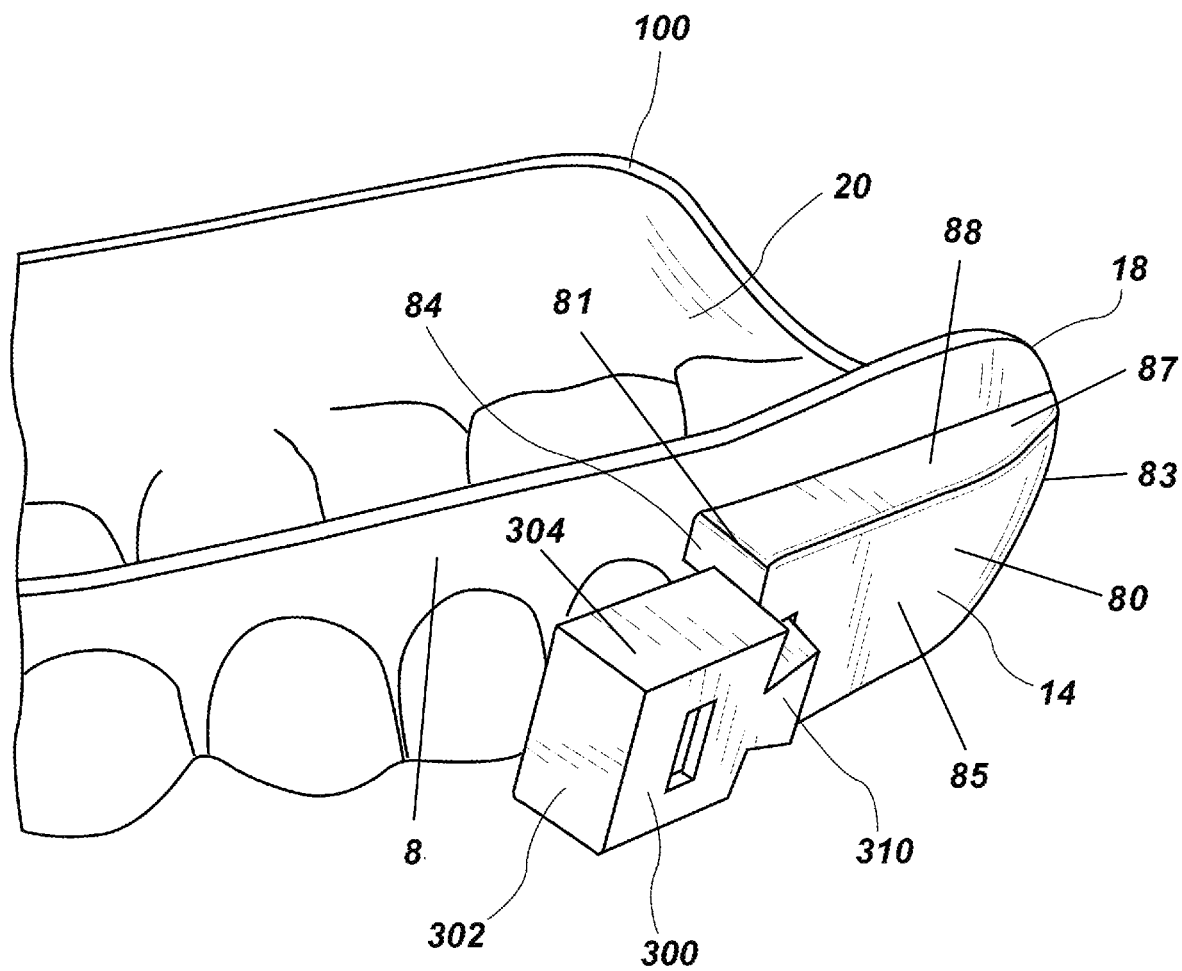
FIG. 6 is a right side, lower perspective view of the posterior portion of the upper appliance shown in FIG. 4, with the insert portion partially removed.
Figure 7:
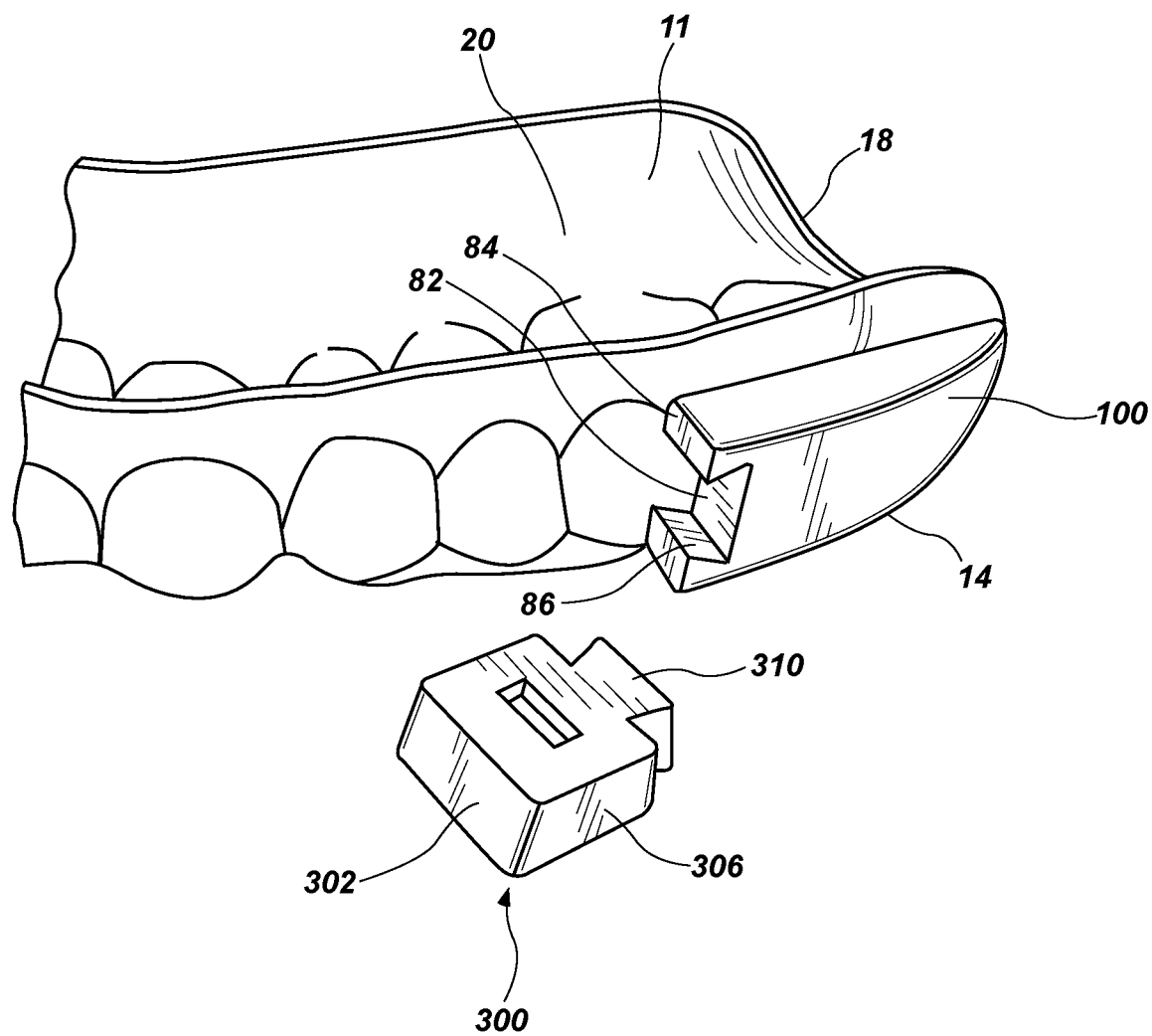
FIG. 7 is a right side, lower perspective view of the posterior portion of the upper appliance shown in FIG. 4, with the insert portion completely removed.

The present invention comprises an oral appliance (10) for treating snoring and/or sleep apnea in a subject and which also accomplishes orthodontic treatment, either by itself or in conjunction with orthodontic trays. The device generally comprises at least an upper dental tray, a lower dental tray, and a pair of mechanical inserts. The upper tray (100) has an anterior portion (16), a posterior portion (18), a right side (12), a left side (14), a buccal side (8), a lingual side (9), coronal surface (130), an interior surface (11), and an exterior surface (13). The upper tray (100) further includes a receptacle (20) bounded by the interior surface (11) of the upper tray (100) and a pair of lateral projections (80).

On the right side of the upper tray, a right side lateral projection (87) is connected to the buccal side (8) of the right side of the upper tray (100) in a posterior portion (18) of the upper tray (100) and has an anterior end (81) having an engagement surface (84), a posterior end (83), an upper surface (88), a lower surface (91), and a lateral surface (85). The anterior end (81) of the right side lateral projection (87) is configured to be reversibly attached to the posterior end (310) of a right side insert (300) which further comprises a first lateral surface (304), a second lateral surface (306), and an anterior end (302).

On the left side of the upper tray, a left side lateral projection is connected to the buccal surface (8) of the left side of the upper tray (100) in a posterior portion (18) of the upper tray (100) and includes an anterior end (81) having an engagement surface (84), a posterior end (83), an upper surface (88), a lower surface (91), and a lateral surface (85). The anterior end (81) of the left side lateral projection (87) is configured to be reversibly attached to the posterior end (310) of a left side insert (300) which further comprises a first lateral surface (304), a second lateral surface (306), and an anterior end (302).

Preferably, the posterior end (310) of each insert (300) is reversibly attached to the anterior end (81) of a respective lateral projection (80) through an interference fit. For example, the anterior end (81) of each lateral projection (80) can comprise a recess, and the posterior end (310) of each insert (300) can comprise a rearward projection adapted to fit within the recess and thereby secure the insert (300) to a respective lateral projection (80). The rearward projection can be a wedge having sides that extend laterally and posteriorly, in which case the recess is wedge-shaped and configured to receive and retain the projection in a tongue-and-groove fashion. In a further embodiment, the invention can include a plurality of pairs of inserts (300), with at least some of the insert pairs having lateral sides which are different in length than the lateral sides of other insert pairs. This allows customization of the positioning of the upper jaw of a user with respect to the user's lower jaw during use of the present appliance.

The lower tray (200) of the appliance has an anterior portion (16), a posterior portion (18), a right side (12), a left side (14), a buccal side (8), a lingual side (9), coronal surface (230), an interior surface (11), and an exterior surface (13), and like the upper tray includes a receptacle (20) bounded by the interior surface (11) of the lower tray (100). The lower tray further includes a pair of upwardly extending projections (50) which contact the anterior ends (302) of respective inserts (300). Specifically, the lower tray comprises a right side upwardly extending projection (50) having a proximal end (52), a distal end (54), an interior surface (51), an exterior surface (53), an anterior side (56), and a posterior side (58), with the projection (50) being connected at the proximal end (52) to the right side of the lower tray (200) and extending upwardly therefrom, and a left side upwardly extending projection (50) having a proximal end (52), a distal end (54), an interior surface (51), an exterior surface (53), an anterior side (56), and a posterior side (58), the left side upwardly extending projection (50) being connected at the proximal end (52) to the left side of the lower tray (200) and extending upwardly therefrom. The lower projections are generally positioned in an anterior portion of the upper tray (200). The posterior side (58) of the right side upwardly extending projection (50) faces the anterior surface (302) of the right side insert (300) of the right side of the upper tray (100) when the appliance is worn by a user, and the posterior side (58) of the left side lower projection faces the anterior surface (302) of the left side insert (300) of the left side of the upper tray (100).

In order to alleviate snoring and/or apnea in a user, the anterior surface of the right side insert comprises an engagement surface which contacts the posterior surface of the right side lower projection, and the anterior surface of the left side insert comprises an engagement surface which contacts the posterior surface of the left side lower projection, thereby limiting the forward positioning of the upper tray (100) with respect to the lower tray (200) when in use. In order to accomplish orthodonture, the receptacles (20) of the upper tray (100) and the lower tray (200) are each configured either to receive and retain an orthodontic tray (400), or to reposition one or more teeth of a subject and/or to change the configuration of a subject's mandible and/or maxilla when the appliance is worn by the subject.

In a preferred embodiment, the invention includes a first orthodontic tray (402) and a second orthodontic tray (404), with each of the orthodontic trays (400) having an inner surface (403) for contacting at least some of a subject's teeth and an outer surface (405). The orthodontic trays (400) can be received within respective receptacles (20) such that the outer surface (405) of a respective orthodontic tray (400) contacts the interior surface (11) of a respective receptacle (20). The orthodontic trays can comprise a series of first orthodontic trays and a series of second orthodontic trays, with each of the orthodontic trays in the series comprising a different configuration, in order to change the position of a subject's teeth and/or the shape of the subject's jaw. In these embodiments, the receptacles (20) of the upper tray (100) are shaped to receive all of the first orthodontic trays (402), and the receptacles (20) of the lower tray (200) are shaped to receive all of the second orthodontic trays (404).

In preferred embodiments, the upper tray (100) comprises an upper incisal surface (101) and the lower tray (200) comprises a lower incisal surface (201), and at least a portion of the upper incisal surface (101) and lower incisal surface (201) are not in contact when the coronal surface (130) of the upper tray (100) contacts the coronal surface (230) of the lower tray (200) in a posterior portion of the appliance, thereby forming an anterior opening (76) and allowing a flow of air through the anterior opening (76) during use.

DESCRIPTION

Definitions

As used herein, the following terms and variations thereof have the meanings given below, unless a different meaning is clearly intended by the context in which such term is used. Directions, locations, and orientations (e.g., "downward," "horizontal," "anterior") which are described below with reference to a subject can also refer to the direction or placement of the present appliance or a portion thereof when the appliance is worn by a subject.

"Anterior" means in the direction of or toward or adjacent the front portion (opening) of a subject's mouth.

"Apnea" and "sleep apnea" refer to a temporary cessation of breathing and/or to instances of shallow or infrequent breathing during sleep, generally caused by a blockage of a subject's airway (referred to as obstructive sleep apnea).

"Axial plane" refers to an imaginary plane that divides the body into cranial and caudal (upper and lower) portions.

"Buccal" means in the direction of or toward a subject's cheek. In relation to a subject's teeth, this refers to the side of the teeth facing the cheek.

"Coronal plane" refers to a hypothetical planar surface that extends through the body from the head to the feet, and divides the body into front and rear halves.

"Coronal" refers to a position or direction which is on or toward the distal end of a tooth (i.e., where the biting surface is located). A coronal surface is thus the biting surface of a tooth, which in posterior teeth is generally referred to as an occlusal surface and on anterior teeth is called an incisal surface. "Coronal surface" may also refer to the corresponding surface of a dental tray which contacts the other dental tray when the present device is worn by a user, i.e. to a lower surface of an upper dental tray or to an upper surface of a lower dental tray.

"Dental tray" refers to a structure comprising a receptacle for receiving the teeth of a subject. In some embodiments, the receptacle of the dental tray has an opening for receiving teeth and an interior surface which contacts the subject's teeth directly. In other embodiments, the receptacle receives an orthodontic tray.

"Downward" and "downwardly" mean in the direction of or toward a lower portion of a subject's body. "Upward" and "upwardly" mean in the opposite direction, i.e. in the direction of or toward an upper portion of a subject's body.

"Elongated" refers to a configuration or shape having a length which is longer than its width.

"Horizontal," with respect to the present appliance, refers to disposition in a plane approximately perpendicular to the sagittal and/or the coronal plane of a subject, i.e. within 15 degrees of such a perpendicular plane.

"Labial" means in the direction of, toward, or adjacent to a subject's lips. In relation to a subject's teeth, this refers to the side of the front teeth facing the lips.

"Lateral" means away from the sagittal plane of a subject. "Laterally" refers to a position or direction placed or extending away from the sagittal plane of a subject.

"Left" means to the left of the center sagittal plane of a subject, from the perspective of the subject.

"Lingual" means in the direction of, toward, or adjacent to a subject's tongue. In relation to a subject's teeth, this refers to the side of the teeth facing the tongue.

"Lower" refers to the relative position of a component in the present appliance which is closer to or toward a lower portion of a subject's body when the component is being used.

"Mandibular" refers to the lower jaw.

"Mandibular dentition" refers to the teeth of the lower jaw.

"Maxillary" refers to the upper jaw.

"Maxillary dentition" refers to the teeth of the upper jaw.

"Mechanically connected" means physically connected, either through a connection based on direct physical contact or via another intermediate mechanical structure.

"Medial" means toward the center sagittal plane of a subject.

"Orthodontic" refers to a feature or component of an appliance, or an appliance itself, which repositions the teeth and/or jaw(s) of a subject.

"Orthodontic tray" refers to a dental tray for receiving the upper or lower dentition of a subject. An interior surface of an orthodontic tray contacts the subject's teeth directly with sockets or depressions sized to receive a subject's teeth.

"Posterior" means in the direction of or toward or adjacent the rear portion of a subject's mouth.

"Right" means to the right of the center sagittal plane of a subject, from the perspective of the subject.

"Sagittal plane" refers to an imaginary plane that travels vertically from the top to the bottom of the body of a subject, dividing it into left and right portions.

"Subject" refers to a user of the present appliance, usually a human user.

"Thermoplastic" refers to a material, generally a polymer material, which may be softened by heat and hardened by cooling in a reversible physical process. The thermoplastic materials used in some components of the present appliance retain their shape at 100° F. and preferably become soft (deformable) at a temperature of 212° F. or below.

"Tray" and "dental tray," as used herein, refer to a generally U-shaped portion of the present appliance comprising an open area for receiving the maxillary or mandibular teeth of a subject, as the case may be.

"Upper" refers to the relative position of a component in the present appliance which is closer to or toward an upper portion of a subject's body when being used.

"Vertical," with respect to the present appliance, refers to disposition in a plane approximately parallel to the sagittal and/or the coronal plane of a subject, i.e. within 15 degrees of such a parallel plane. Preferably, vertical refers to a direction toward or away from a subject's head or feet.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Oral Appliance

FIG. 1 illustrates an embodiment of the present sleep apnea oral appliance. The present appliance 10 generally comprises a pair of dental trays 15, an upper tray 100 and a lower tray 200, which cooperate to position a subject's jaws so as to treat or avoid sleep apnea. The upper tray 100 is fitted onto a subject's maxillary dentition, while the lower tray 200 is fitted to the subject's mandibular dentition. The tray portions 15 of the present device have a buccal surface 8, a lingual surface 9, an interior surface 11, an exterior surface 13, a right side 12, a left side 14, an anterior portion 16, and a posterior portion 18, and each comprise a generally U-shaped tooth-receiving receptacle 20 formed on one horizontal side of the tray 15 to fit over a subject's dentition, in the manner of conventional orthodontic devices.

In one embodiment, the receptacle 20 is configured to receive the teeth of a subject and to contact the subject's teeth on the interior surface 11 of the tray 15. The receptacle 20 comprises lateral contiguous walls 23 extending from a bottom surface 21 facing the coronal surfaces of a subject's teeth toward the maxilla or mandible, as the case may be, i.e. buccal wall 22 and labial wall 24, so as to cover some or all of the buccal and labial sides of some or all of a subject's teeth. The trays 15 can be formed to conform to a subject's pre-existing dentition, or in a preferred embodiment can be formed to receive orthodontic trays 400 to accomplish a change in the existing dentition and/or in the shape of a subject's mandible and/or maxilla, as described further below.

The exterior portions of the trays 15 comprise a coronal surface 30 formed on the horizontal side of the tray opposite the receptacle 20, i.e. on the exterior surface 13 of the tray 15. The coronal surface 130 of the upper tray 100 contacts the coronal surface 230 of the lower tray 200 in the posterior portion 18 of the right and left sides of the appliance 10, approximately in the molar area of a user's dentition. Preferably, when the coronal surface 130 and the coronal surface 230 are in contact with each other, when worn by a user, at least a portion of the anterior coronal surfaces of the upper tray 100 and lower tray 200 (i.e., the upper incisal surface 101 and lower incisal surface 201) are not in contact, thereby providing an anterior opening 76 between the upper incisal surface 101 and lower incisal surface 201 in the anterior portion 16 of the device 10. The anterior opening 76 allows a flow of air therethrough during use. Maintaining a subject's mouth in a slightly open position by separating the upper and lower jaws in this way also helps to treat apnea.

In the illustrated embodiments, each lateral side of the lower tray 200 comprises an upwardly extending projection 50. The projection 50 extends distally from the coronal surface 30 of the lower tray 200, i.e. upwardly when worn by a subject wearing the present device 10. The distal end (distal side) 54 of the projection extends upwardly beyond the coronal surface 130 of the upper tray 100 when worn by a subject, such that a portion of the distal end 54 of the projection 50 is positioned laterally with respect to an exterior surface 13 of one lateral side of the upper tray 100. An interior surface 51 of each of the projections 50 thus touches or is adjacent to an exterior surface 13 of the upper tray 100 on the right side 12 or left side 14, as the case may be. This positioning helps to limit the lateral movement of the upper and lower jaws when the present appliance 10 is worn by a user and provides lateral stability.

A proximal (lower) end 52 of the projection 50 connects to the coronal surface 30 of the lower tray 200 at a middle portion of the lower tray, posteriorly with respect to the anterior opening 76 but anteriorly with respect to the posterior portion or end 18 of a respective lateral side of the lower tray 200. The projection 50 further includes an anterior side 56 and posterior side 58. The posterior side 58 preferably comprises a relatively flat or planar rearwardly-facing surface for contacting a corresponding front-facing engagement surface (anterior end) 302 of an insert 300 of the upper tray 100. When the present appliance 10 is worn by a user, the posterior side 58 of the projection contacts the anterior surface 302 of the insert 300 in order to limit (stop) anterior movement of the upper jaw (maxilla) and corresponding posterior movement of the lower jaw (mandible), thereby maintaining the user's jaws in an orientation conducive to preventing or ameliorating sleep apnea.

Figure 9:
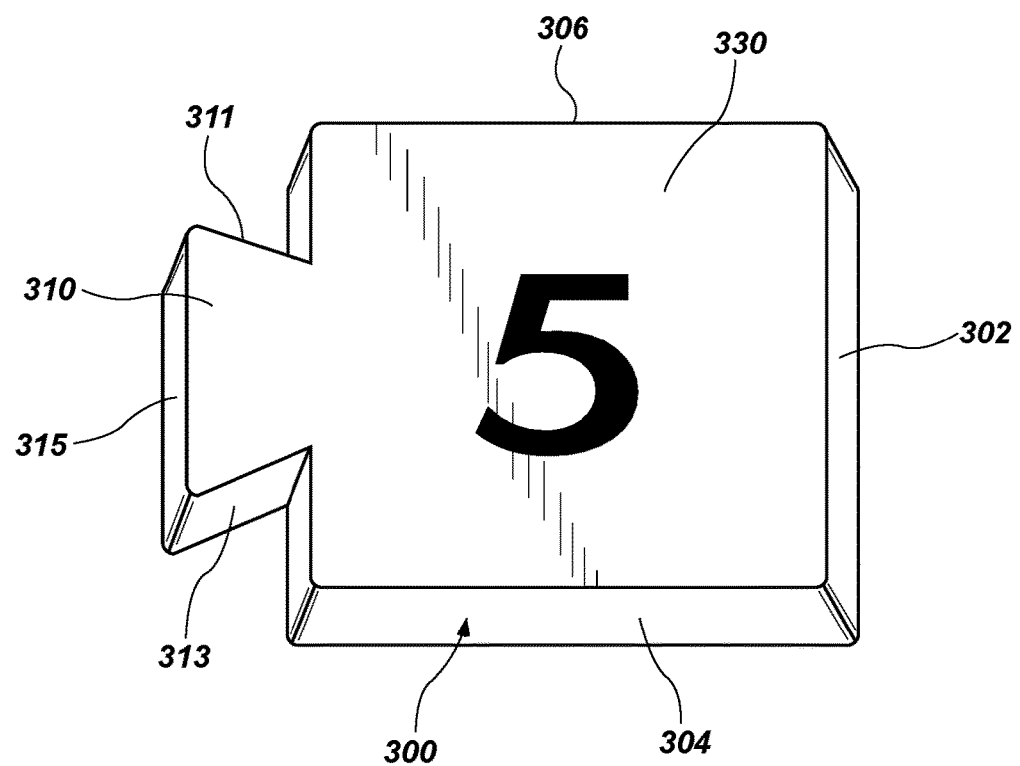
FIG. 9 is a top perspective view of one of the inserts of FIG. 8.
Figure 10:
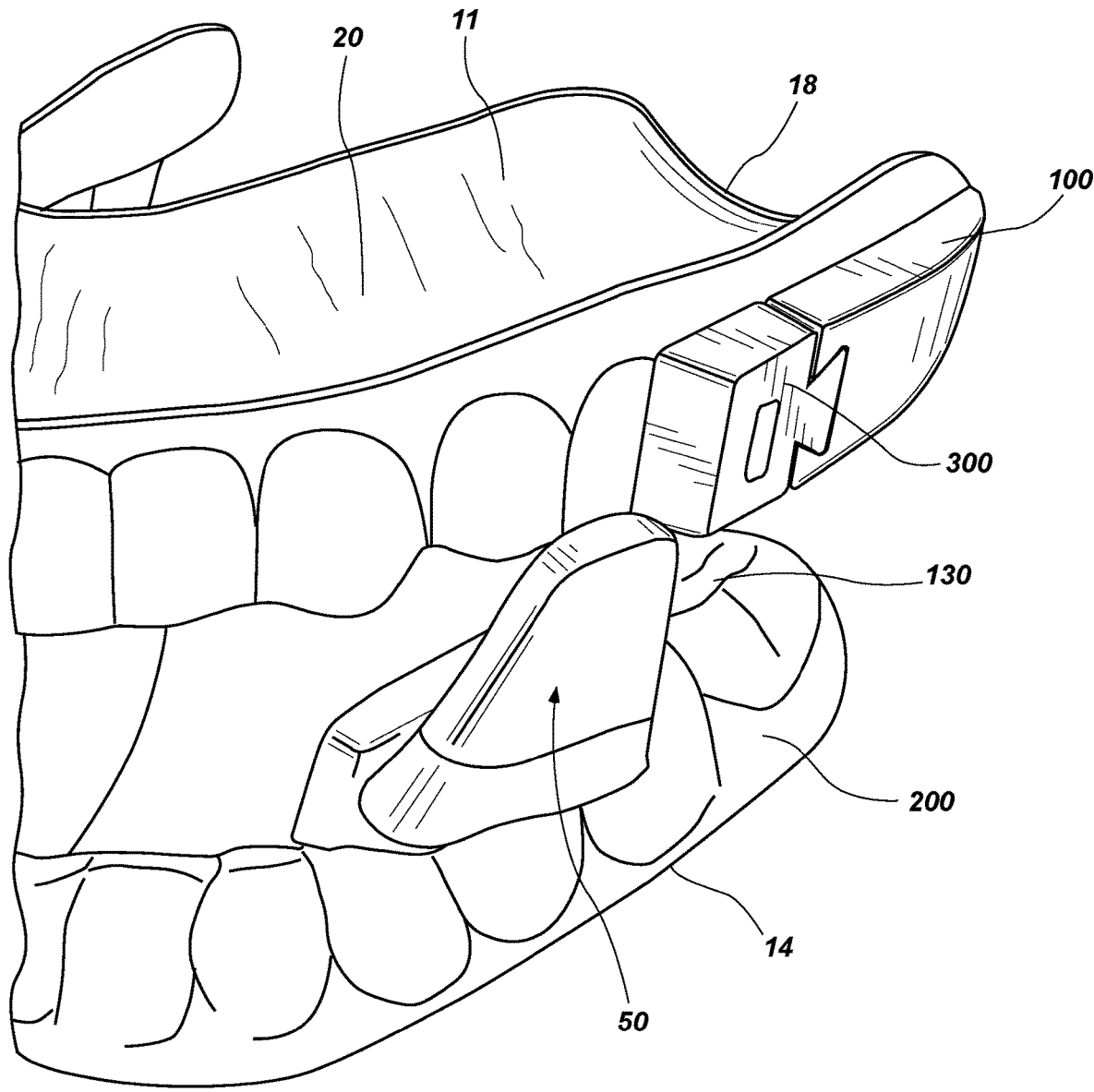
FIG. 10 is a left side, upper perspective view of the left side of the upper and lower portions of the present appliance, partially detached from one another.
Figure 11:
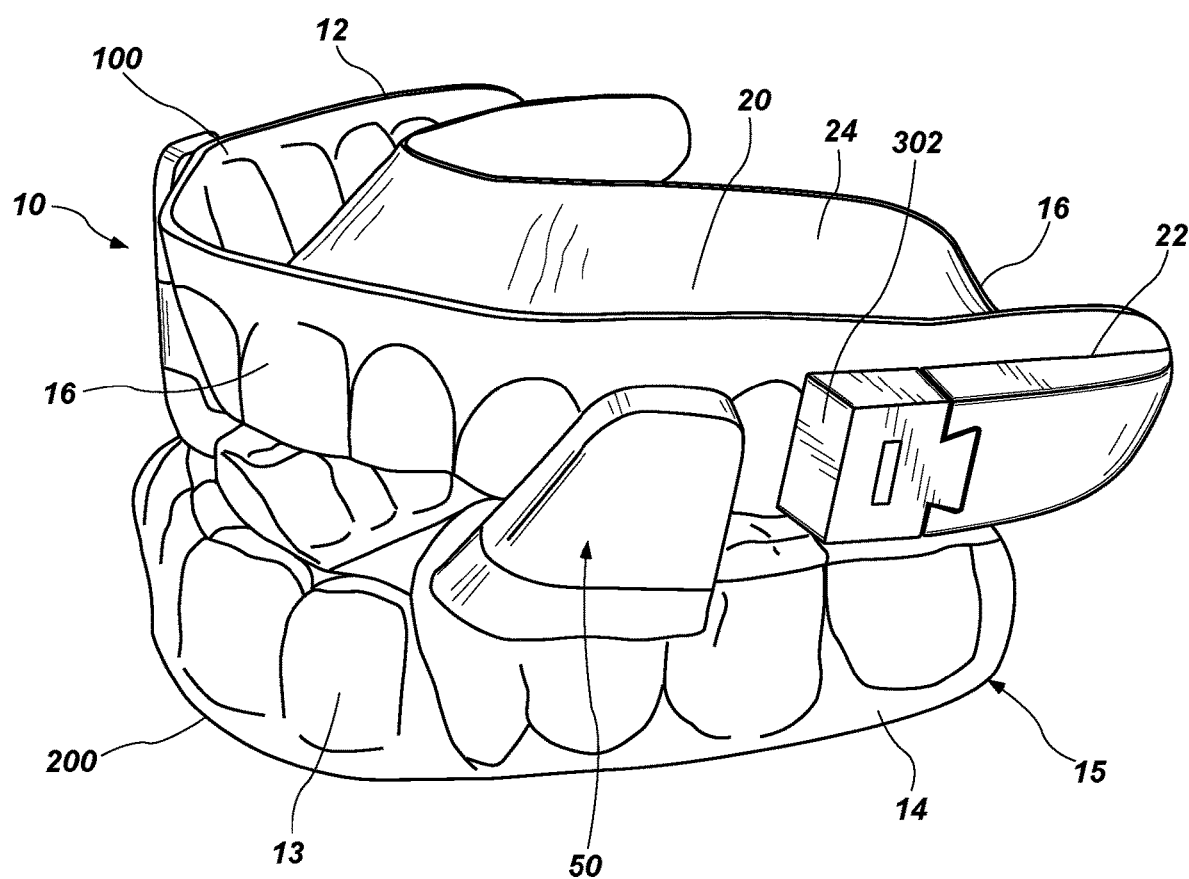
FIG. 11 is a left side, elevation view of the upper and lower portions of the present appliance, partially detached from one another.

A unique feature of the present oral appliance 10 is the use of laterally positioned axial inserts 300. The inserts 300 are configured to attach to each lateral side of the upper tray 100 and to engage the posterior side 58 of the upward projection 50 of the lower tray 200 at an engagement surface 302 of the insert 300. As shown in FIG. 9, each insert 300 comprises an engagement surface 302, first and second lateral sides 304 and 306, and an attachment end (posterior end) 310 opposite the engagement surface (anterior end) 302. The insert 300 further comprises an inner surface which contacts or is adjacent to a respective lateral exterior surface 13 of the upper tray 100, and an outer surface 330 opposite the outer surface 330. As best seen in FIGS. 4-7, the exterior surface 13 of the right lateral side 12 and the left lateral side 14 of the upper tray 100 each comprises a lateral projection 80, i.e. right side lateral projection 87 and left side lateral projection 89. Each lateral projection 80 preferably comprises an anterior end 81 having an engagement surface 84, a posterior end 83, an upper surface 88, a lower surface 91, and a lateral surface 85. A medial side of the lateral projection 80 is connected to the buccal surface 8 of the upper tray 100 (either through mechanical or chemical attachment or through integral molding with the upper tray 100) in a posterior portion of the upper tray 100.

The anterior-facing engagement surface 84 of the lateral projection 80 is designed to cooperate with the engagement surface 302 of the insert 300 of the upper tray 100 so as to mechanically retain the insert 300 on the upper tray 100. The posterior, attachment end 310 and the anterior, connecting end 81 are preferably provided with mutually fitting locking elements in order to retain the insert 300 on the upper tray 100. In the illustrated embodiments, the attachment end 310 of the insert 300 engages with the connecting end 84 of the upper tray 100 in a tongue-and-groove fashion, such that a laterally flaring wedge 312 fits within a recess 86 formed in the connecting end 84. As will be apparent to one of skill in the art, the insert 300 could alternatively be provided with a groove and the connecting end 84 could be configured with a forwardly projecting "tongue," or other configurations can be supplied to mechanically attach the insert 300 to the upper tray 100. In the illustrated environments, the sides 311, 313, and 315 of the wedge 312 preferably form an interference fit with the groove or recess 86 in order to securely retain the insert 300 in the present appliance 10. In a preferred embodiment, the insert 300 is formed from an elastomeric material, and the tongue of the attachment end 310 is formed with slightly larger dimensions than the recess 86, so that when the tongue is urged into the recess 86, it exerts an outward force that helps to retain it within the recess 86. Once attached to the upper tray 100, the forward-facing engagement surface 302 of the insert 300 is positioned to contact the rearward-facing posterior side 58 of the projection 50 when the present appliance 10 is worn by a user.

The insert engagement surface 302 and the posterior side 58 of the projection 50 preferably have angled opposed surfaces that interact to serve as advancement engagement surfaces for the mandible, i.e., the insert engagement surface 302 and the posterior side 58 of the projection 50 are not vertical and are disposed at angle to the coronal plane of a subject when the appliance is worn. Both the posterior face (posterior side 58) and the anterior face (engagement surface 302 of the insert) may be angled, to assist in advancing the mandible as the trays 15 vertically close, employing a camming action. The engagement surface of the posterior side 58 is preferably disposed at a non-vertical angle with an upward and forward slant, though a vertical or other interface between the insert engagement surface 302 and the projection 50 are also possible.

Figure 8:
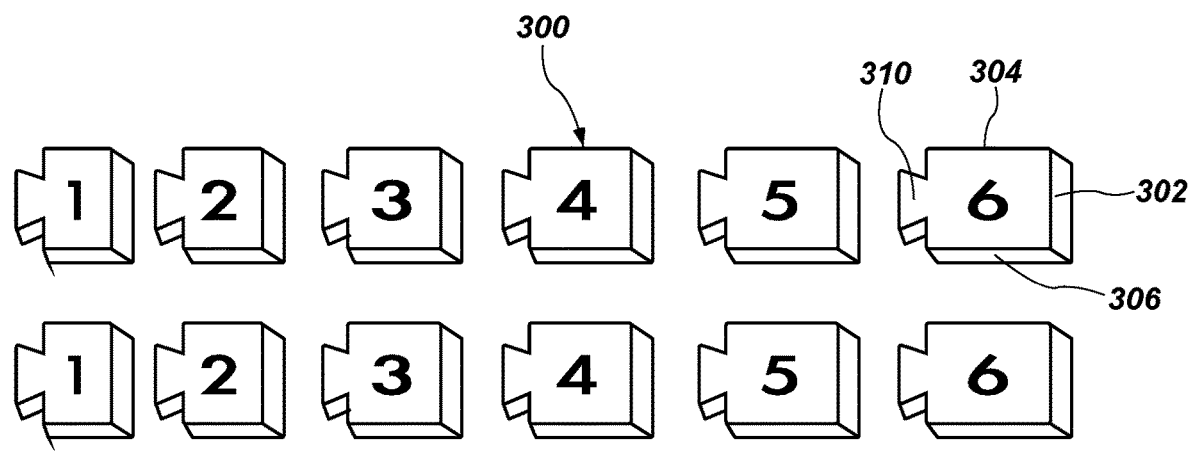
FIG. 8 is a top perspective view of a set of inserts for use with the upper portion of the present appliance.

In order to be able to adjust the relative position of a user's maxilla and mandible when the present appliance 10 is worn, inserts 300 of different lengths can be used. As shown in FIG. 8, the inserts 300 can be formed with lateral sides 304, 306 of different lengths, such that the engagement surfaces 302 of different inserts extend further forward or rearward, depending on the need of the user. In FIG. 8, the inserts labeled "1" through "6" comprise lateral sides 304, 306 of increasing length. As a result, a user's mandible can be positioned relatively anteriorly through the use of higher-numbered inserts, i.e. with longer lengths, or can be positioned relatively posteriorly through the use of lower-numbered inserts with shorter sides. A set of inserts can be provided for use with the present appliance 10 having lateral sides that differ in increments of 1 mm, increments of 0.5 mm, or increments of 0.25 mm, for example. For this reason, attachment of the inserts 300 to the upper tray 100 via a mechanical connection is preferred, so that the attachment is reversible, and can be changed as needed. Preferably, the first lateral side 304 is coplanar with the upper surface 88 of the lateral projection 80, and the second lateral side 306 is coplanar with the lower surface 91 of the lateral projection 80, for patient comfort.

The present appliances 10 can be formed from a variety of orally compatible materials, typically polymers, used to form orthodontic appliances. In one embodiment, acrylic is used to form the present appliance. Thermoplastic polymers, thermosets, thermoplastic elastomers, and other materials can also be used. When thermoplastic materials are used, they must be capable of retaining their shape when used by a subject, and thus preferably remain solid at least at about 100° F., and preferably remain solid at somewhat higher temperatures, such as at 110° F., 120° F., or higher. When thermoplastic materials are used to form the present trays, they preferably become deformable at a temperature of 212° F. or less, so that they can be made plastic by being placed in boiling water. Preferably, the material is not deformable at less than 120° F., preferably at not less than 145° F.

In an alternative embodiment, the features of the upper tray and lower tray can be reversed, i.e. such that the upwardly extending projection (50) on the lower tray (200) becomes an downwardly extending projection on the upper tray (100). This embodiment can be viewed by taking the embodiment shown in FIGS. 1-10 and placing it upside down, and features of this embodiment can likewise be understood as being positioned upside-down with respect to the embodiment illustrated in FIGS. 1-10.

The lower tray has an anterior portion, a posterior portion, a right side, a left side, a buccal side, a lingual side, a coronal surface, an interior surface, and an exterior surface. The lower tray further includes a receptacle bounded by the interior surface of the lower tray and a pair of lateral projections. On the right side of the lower tray, a right side lateral projection is connected to the buccal side of the right side of the lower tray in a posterior portion of the lower tray and has an anterior end having an engagement surface, a posterior end, a lower surface, an upper surface, and a lateral surface. The anterior end of the right side lateral projection is configured to be reversibly attached to the posterior end of a right side insert which further comprises a first lateral surface, a second lateral surface, and an anterior end. On the left side of the lower tray, a left side lateral projection is connected to the buccal surface of the left side of the lower tray in a posterior portion of the lower tray and includes an anterior end having an engagement surface, a posterior end, a lower surface, an upper surface, and a lateral surface. The anterior end of the left side lateral projection is configured to be reversibly attached to the posterior end of a left side insert which further comprises a first lateral surface, a second lateral surface, and an anterior end. As with the illustrated embodiments, the posterior end of each insert preferably is reversibly attached to the anterior end of a respective lateral projection through an interference fit.

The upper tray of the appliance has an anterior portion, a posterior portion, a right side, a left side, a buccal side, a lingual side, coronal surface, an interior surface, and an exterior surface, and like the lower tray includes a receptacle bounded by the interior surface of the upper tray. The upper tray further includes a pair of downwardly extending projections which contact the anterior ends of respective inserts. Specifically, the upper tray comprises a right side downwardly extending projection having a proximal end, a distal end, an interior surface, an exterior surface, an anterior side, and a posterior side, with the projection being connected at the proximal end to the right side of the upper tray and extending downwardly therefrom, and a left side upper projection having a proximal end, a distal end, an interior surface, an exterior surface, an anterior side, and a posterior side, the left side upper projection being connected at the proximal end to the left side of the upper tray and extending downwardly therefrom. The upper projections are generally positioned in an anterior portion of the lower tray. The posterior side of the right side upper projection faces the anterior surface of the right side insert of the right side of the lower tray when the appliance is worn by a user, and the posterior side of the left side upper projection faces the anterior surface of the left side insert of the left side of the lower tray.

In order to alleviate snoring and/or apnea in a user, the anterior surface of the right side insert comprises an engagement surface which contacts the posterior surface of the right side upper projection, and the anterior surface of the left side insert comprises an engagement surface which contacts the posterior surface of the left side upper projection, thereby limiting the forward positioning of the lower tray with respect to the upper tray when in use. In order to accomplish orthodonture, the receptacles of the lower tray and the upper tray are each configured either to receive and retain an orthodontic tray, or to reposition one or more teeth of a subject and/or to change the configuration of a subject's mandible and/or maxilla when the appliance is worn by the subject.

Orthodontic Trays

In one embodiment, the trays 15 can be formed as a series of orthodontic dental trays for use by a subject. In this embodiment, a set of upper and lower trays 100, 200 having differently-configured receptacle portions 20 can be applied to the subject over time in order to reposition individual teeth in successive steps and/or to change the configuration of a subject's mandible and/or maxilla. The successive use of a number of such dental trays 15 permits each appliance to be configured to move individual teeth in small increments, typically less than 2 mm, preferably less than 1 mm, and more preferably less than 0.5 mm (referring to the maximum linear translation of any point on a tooth as a result of using a single appliance). The use of the inserts 300 of the present appliance 10 provides a great advantage when orthodontic trays are used in the present invention, because an optimum relative position of the mandible and maxilla of a user can be provided using an insert having a desired length, thereby addressing a user's sleep apnea while allowing orthodonture.

In this embodiment, the tooth-receiving receptacle portions 20 of the dental trays 15 typically have a geometry corresponding to an intermediate or end tooth arrangement intended for a subject. When such a tray 15 is first worn by the subject, certain of the teeth will be misaligned relative to an undeformed geometry of the receptacle portion 20 of a tray 15. In this embodiment, the tray 15 is formed from a material that is sufficiently resilient to accommodate or conform to the misaligned teeth, but will apply sufficient resilient force against such misaligned teeth to reposition the teeth to the intermediate or end arrangement desired for that treatment step. The appliance will preferably, but not necessarily, fit over all teeth present in the upper or lower jaw. In some cases only certain teeth will be repositioned while will provide a base or anchor region for holding the repositioning appliance in place as it applies the resilient repositioning force against the tooth or teeth to be repositioned A subject's teeth are repositioned from an initial tooth arrangement to a final tooth arrangement by placing a series of incremental position adjustment appliances in the subject's mouth. The first tray appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the subject's mouth, where the final appliance has a geometry selected to progressively reposition teeth from the last intermediate arrangement to the final tooth arrangement.

In order to design a series of dental trays 15 that will reposition a particular subject's teeth, a digital data set representing an initial tooth arrangement and a final tooth arrangement can be determined. The initial data set representing the initial tooth arrangement, which can be presented as a visual image, is manipulated to reposition individual teeth. A final digital data set is then produced which represents the final tooth arrangement with repositioned teeth. The initial digital data set may be provided by conventional techniques, including digitizing X-ray images, images produced by computer-aided tomography (CAT scans), images produced by magnetic resonance imaging (MRI), and/or by other methods known to the art for producing three-dimensional digital representations of a subject's teeth. Alternatively, the initial digital data set may be provided by producing a plaster cast of the subject's teeth (prior to treatment) by conventional techniques, for example, and the plaster cast can then be scanned using laser or other scanning equipment to produce a high resolution digital representation of the plaster cast of the subject's teeth.

Once the initial and final data sets have been determined, a series of intermediate data sets, representing intermediate tooth positions for a subject's teeth, are determined. The successive intermediate digital data sets are preferably produced by determining positional differences between selected individual teeth in the initial data set and in the final data set and interpolating the differences. Such interpolation may be performed over at least three discrete stages, embodied in three different dental trays, more often at least ten, sometimes at least twenty-five, and occasionally forty or more. The interpolation can be a linear interpolation for some or all of the positional difference, or alternatively may be nonlinear. The positional differences will correspond to tooth movements where the maximum linear movement of any point on a tooth is preferably 2 mm or less, usually 1 mm or less, and preferably 0.5 mm or less.

Once the intermediate and final data sets have been determined, the appliances can be fabricated, such as with a rapid prototyping device or digital printer. Preferably, the appliance is polymeric and is formed from a thin sheet of a suitable elastomeric polymeric, such as Tru-Tain 0.03 in. thermal forming dental material (Tru-Tain Plastics, Rochester, Minn. 55902). One structure corresponding to each of the dental tray appliances is produced.

The foregoing dental tray appliances and their use in orthodontic treatment are described in U.S. Pat. No. 5,975,893 and in other patents assigned to Align Technology, Inc., including U.S. Pat. Nos. 6,215,62, 6,217,325, 6,398,548, 6,626,666, 6,629,840, 6,699,037, 7,134,874, 7,474,307, 8,105,080, and 8,562,340.

Figure 12:
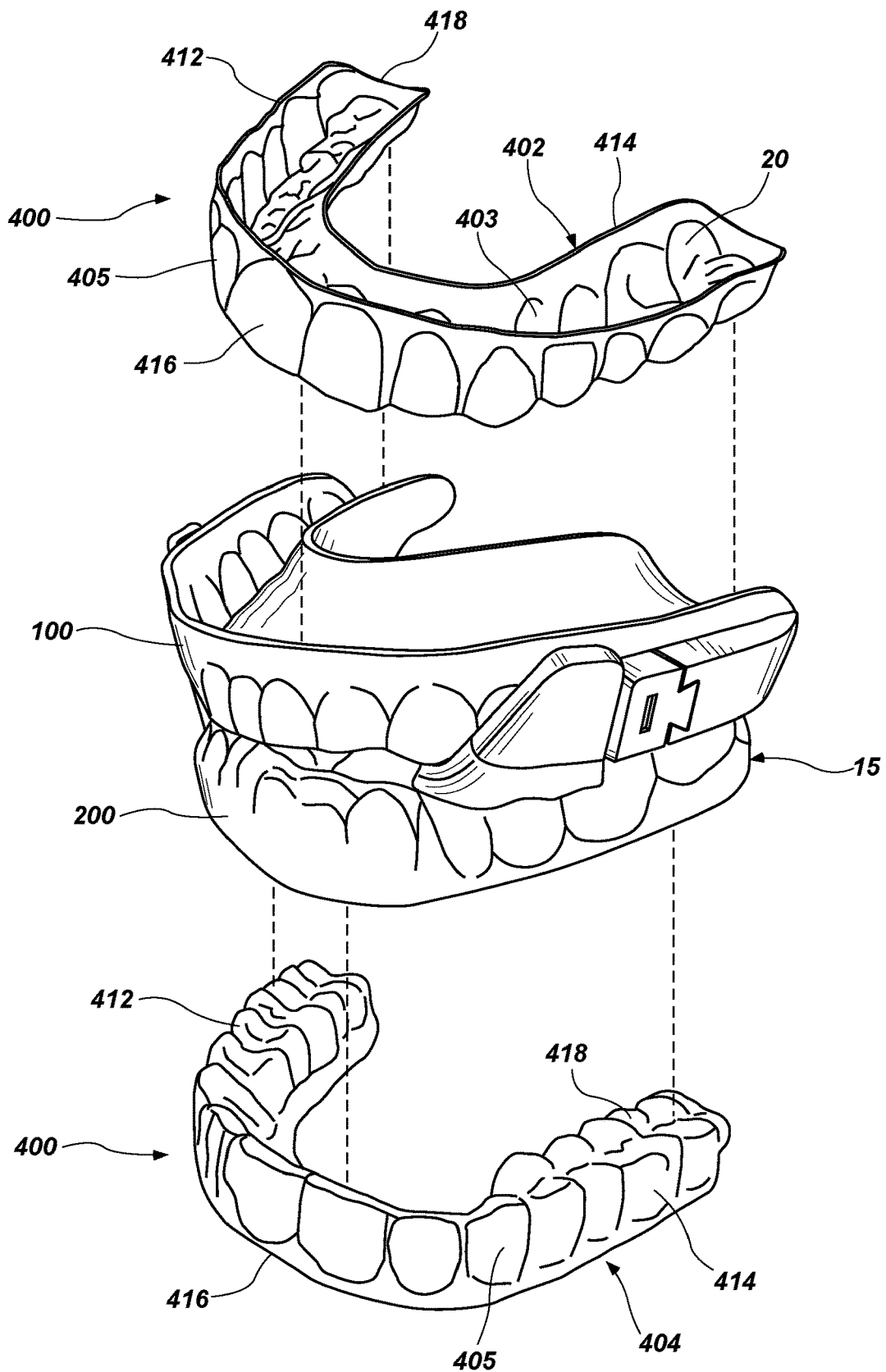
FIG. 12 is a left side, upper perspective view of two orthodontic trays and their placement into the upper and lower portions of the present appliance.

In another embodiment, shown in FIG. 12, the present trays 15 can be designed to be used in combination with a set of separately formed orthodontic trays 400, typically formed from a polymer material. The orthodontic trays 400 can be formed as a series of orthodontic dental trays in the manner described above for upper and lower trays of the present invention which have differently-configured receptacle portions, and are likewise applied to a subject over time in order to reposition individual teeth in successive steps and/or to change the configuration of a subject's mandible and/or maxilla. Such trays are available commercially from Align Technology (San Jose, Calif.) as INVISALIGN orthodontic trays. In this embodiment, the interior surfaces 11 of the upper tray 100 and lower tray 200 (i.e. the receptacles 20) are each configured to receive outer surfaces 405 of respective orthodontic trays 400.

As shown in FIG. 12, the set of orthodontic trays 400 comprise at least an upper tray 402 and a lower tray 404 for use with the present appliance. Each of such orthodontic trays 400 usually comprises an inner surface 403 for contacting at least some of a subject's teeth, an outer surface 405, an anterior portion 416, a posterior portion 418, a right side 412, and a left side 414. In this embodiment, the receptacle 20 of the present appliance 10 is sized to receive and reversibly retain an orthodontic tray 400, generally by contacting an outer surface 405 of an orthodontic tray 400. In this way, a subject can use the orthodontic trays 400 during the day and then continue using them at night in combination with the present appliance 10 in order to obtain relief from sleep apnea.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All patents, patent applications, and other references cited herein are incorporated by reference in their entirety.

What is claimed is:

1. An oral appliance for treating snoring and/or sleep apnea in a subject, comprising:
   (1) an upper tray having an anterior portion, a posterior portion, a right side, a left side, a buccal side, a lingual side, coronal surface, an interior surface, and an exterior surface, the upper tray comprising:
      (a) a receptacle bounded by the interior surface of the upper tray;
      (b) a right side lateral projection comprising an anterior end having an engagement surface, a posterior end, an upper surface, a lower surface, and a lateral surface, wherein the right side lateral projection is connected to the buccal side of the right side of the upper tray in the posterior portion of the upper tray;
      (c) a right side insert comprising a first lateral surface, a second lateral surface, an anterior end, and a posterior end, wherein the posterior end is configured to be reversibly attached to the anterior end of the right side lateral projection;
      (d) a left side lateral projection comprising an anterior end having an engagement surface, a posterior end, an upper surface, a lower surface, and a lateral surface, wherein the left side lateral projection is connected to the buccal side of the left side of the upper tray in the posterior portion of the upper tray; and
      (e) a left side insert comprising a first lateral surface, a second lateral surface, an anterior end, and a posterior end, wherein the posterior end is configured to be reversibly attached to the anterior end of the left side lateral projection; and
   (2) a lower tray having an anterior portion, a posterior portion, a right side, a left side, a buccal side, a lingual side, coronal surface, an interior surface, and an exterior surface, the lower tray comprising:
      (a) a receptacle-bounded by the interior surface of the lower tray;
      (b) a right side upwardly extending projection having a proximal end, a distal end, an interior surface, an exterior surface, an anterior side, and a posterior side, the projection being connected at the proximal end to the right side of the lower tray and extending upwardly therefrom, wherein the posterior side of the projection faces an anterior surface of the right side insert of the right side of the upper tray; and
      (c) a left side upwardly extending projection having a proximal end, a distal end, an interior surface , an exterior surface, an anterior side, and a posterior side, the projection being connected at the proximal end to the left side of the lower tray and extending upwardly therefrom, wherein the posterior side of the projection faces an anterior surface of the left side insert of the left side of the upper tray;
   wherein the anterior surface of the right side insert comprises an engagement surface which contacts the posterior side of the right side upwardly extending projection and wherein the anterior surface of the left side insert comprises an engagement surface which contacts the posterior side of the left side upwardly extending projection, thereby limiting the forward positioning of the upper tray with respect to the lower tray alleviating snoring and/or apnea when the oral appliance is used by a subject, wherein the receptacles of the upper tray and the lower tray are each configured to receive and retain an orthodontic tray, or wherein the receptacles of the upper tray and the lower tray are each configured to reposition one or more teeth of a subject and/or to change the configuration of a subject's mandible and/or maxilla when the appliance is worn by the subject, wherein the posterior end of each insert is reversibly attached to the anterior end of a respective lateral projection through an interference fit, wherein the anterior end of each lateral projection comprises a recess and the posterior end of each insert comprises a rearward projection adapted to fit within a respective recess and thereby secure the insert to a respective lateral projection, and when the rearward projection is urged into the recess, the projection exerts an outward force that retains the rearward projection within the recess, and wherein the oral appliance is completely formed from a polymer material.

2. The oral appliance of claim 1, wherein the upper tray comprises an upper incisal surface and the lower tray comprises a lower incisal surface, and wherein at least a portion of the upper incisal surface and lower incisal surface are not in contact when the coronal surface of the upper tray contacts the coronal surface of the lower tray in a posterior portion of the appliance, thereby forming an anterior opening and allowing a flow of air through the anterior opening during use.

3. The oral appliance of claim 1, wherein the rearward projection comprises a wedge having sides that extend laterally and posteriorly and the recess is wedge-shaped and configured to receive and retain the projection in a tongue-and-groove fashion.

4. The oral appliance of claim 1, further comprising a plurality of pairs of inserts, wherein at least some of the insert pairs comprise inserts having lateral sides which are different in length than the lateral sides of other insert pairs.

5. The oral appliance of claim 1, further comprising a first orthodontic tray and a second orthodontic tray, wherein each of the orthodontic trays comprises an inner surface for contacting at least some of a subject's teeth and an outer surface, and wherein the orthodontic trays can be received within respective receptacles of the oral appliance such that the outer surface of a respective orthodontic tray contacts the interior surface of a respective receptacle.

6. The oral appliance of claim 5, wherein the orthodontic trays comprise a series of first orthodontic trays and a series of second orthodontic trays, and wherein each of the orthodontic trays in the series comprises a different configuration in order to change the position of the subject's teeth and/or the shape of the subject's jaw.

7. The oral appliance of claim 6, wherein the receptacles of the upper tray is shaped to receive all of the first orthodontic trays, and the receptacle of the lower tray is shaped to receive all of the second orthodontic trays.

8. A series of oral appliances according to claim 1 for repositioning teeth of a subject, wherein each upper tray and lower tray of the series has a differently-configured receptacle portion corresponding to an intermediate or end tooth arrangement of a subject.

9. A method of treating snoring or sleep apnea in a subject while performing orthodonture, comprising applying the upper trays and lower trays of the series of trays of claim 8 to the subject in order to progressively reposition teeth from an initial tooth arrangement to a final tooth arrangement while treating snoring or sleep apnea in the subject.

* * * * *